United States Patent
Caffey et al.

(10) Patent No.: US 8,050,745 B2
(45) Date of Patent: Nov. 1, 2011

(54) METHODS AND SYSTEMS FOR ENHANCED MEDICAL PROCEDURE VISUALIZATION

(75) Inventors: Sean Caffey, Manhattan Beach, CA (US); Mark Humayun, La Canada Flintridge, CA (US)

(73) Assignee: Doheny Eye Institute, Los Angeles, CA (US)

( * ) Notice: Subject to any disclaimer, the term of this patent is extended or adjusted under 35 U.S.C. 154(b) by 429 days.

(21) Appl. No.: 11/508,734

(22) Filed: Aug. 22, 2006

(65) Prior Publication Data
US 2007/0244367 A1 Oct. 18, 2007

Related U.S. Application Data

(63) Continuation of application No. PCT/US2005/05521, filed on Feb. 22, 2005.

(60) Provisional application No. 60/546,843, filed on Feb. 22, 2004.

(51) Int. Cl.
*A61B 6/00* (2006.01)

(52) U.S. Cl. ........ 600/473; 600/407; 600/475; 436/164; 436/171; 436/169; 436/172; 606/4; 606/5; 606/6; 606/10

(58) Field of Classification Search ............... 600/407, 600/473, 475; 436/164, 171, 63, 169, 172; 606/4–6, 10, 15; 424/9.6
See application file for complete search history.

(56) References Cited

U.S. PATENT DOCUMENTS

| | | | |
|---|---|---|---|
| 3,798,435 A | 3/1974 | Schindl | |
| 5,115,124 A | 5/1992 | Muto et al. | |
| 5,147,354 A * | 9/1992 | Boutacoff et al. | 606/15 |
| 5,570,698 A | 11/1996 | Liang et al. | |
| 5,634,711 A | 6/1997 | Kennedy et al. | |
| 5,733,739 A * | 3/1998 | Zakim et al. | 435/29 |
| 5,818,052 A | 10/1998 | Elabd | |
| 5,993,001 A | 11/1999 | Bursell et al. | |
| 6,178,346 B1 * | 1/2001 | Amundson et al. | 600/473 |
| 6,183,086 B1 | 2/2001 | Neubert | |
| 6,230,046 B1 | 5/2001 | Crane et al. | |
| 6,280,059 B1 | 8/2001 | Ito et al. | |
| 6,357,877 B2 | 3/2002 | Takada | |
| 6,652,452 B1 * | 11/2003 | Seifert et al. | 600/140 |
| 6,934,576 B2 * | 8/2005 | Camacho et al. | 600/473 |
| 7,020,370 B2 | 3/2006 | Harris | |
| 7,048,379 B2 | 5/2006 | Miller et al. | |
| 7,174,094 B2 | 2/2007 | Steinkamp | |
| 7,245,273 B2 | 7/2007 | Eberl et al. | |
| 7,284,861 B2 * | 10/2007 | Fujieda | 351/206 |
| 7,308,296 B2 | 12/2007 | Lys et al. | |

(Continued)

OTHER PUBLICATIONS

International Search Report and Written Opinion for Related PCT Application No. PCT/US08/55277 mailed on Jul. 28, 2008.

(Continued)

*Primary Examiner* — Brian Casler
*Assistant Examiner* — Joel Lamprecht
(74) *Attorney, Agent, or Firm* — Knobbe, Martens, Olson and Bear, LLP

(57) ABSTRACT

The present invention employs image intensification for medical procedures within the human body. Methods and systems of the invention utilize infrared radiation (e.g. greater than about 750 nm) illumination and visualization of a surgical treatment area. Preferred methods and systems of the invention incorporate use of an infrared radiation visualization system which may be known as "night vision" systems.

20 Claims, 2 Drawing Sheets

U.S. PATENT DOCUMENTS

| | | | |
|---|---|---|---|
| 7,311,401 B2 | 12/2007 | Goldfain et al. | |
| 7,420,153 B2 | 9/2008 | Palmer et al. | |
| 7,422,327 B2 | 9/2008 | Smith | |
| 7,499,634 B2 | 3/2009 | Yogesan et al. | |
| 7,654,716 B1 | 2/2010 | Bhadri et al. | |
| 7,677,730 B2 | 3/2010 | Shimizu | |
| 7,762,664 B2 | 7/2010 | Fink | |
| 2002/0025298 A1* | 2/2002 | Blumenkranz et al. | 424/9.6 |
| 2002/0101568 A1 | 8/2002 | Eberl et al. | |
| 2003/0112639 A1 | 6/2003 | Stack | |
| 2003/0218755 A1* | 11/2003 | Wei et al. | 356/497 |
| 2004/0032750 A1 | 2/2004 | Watts et al. | |
| 2004/0181133 A1 | 9/2004 | Al-Ali | |
| 2005/0222499 A1 | 10/2005 | Banik et al. | |
| 2006/0134001 A1* | 6/2006 | Frangioni | 424/9.6 |
| 2006/0152172 A9 | 7/2006 | Mueller et al. | |
| 2008/0029708 A1 | 2/2008 | Olsen et al. | |
| 2009/0016075 A1 | 1/2009 | Bhadri et al. | |
| 2009/0146583 A1 | 6/2009 | Bhadri et al. | |
| 2010/0026957 A1 | 2/2010 | Tanguay, Jr. et al. | |
| 2010/0157620 A1 | 6/2010 | Bhadri et al. | |

OTHER PUBLICATIONS

International Search Report for PCT Application Serial No. PCT/US09/41723 mailed on Oct. 2, 2009.

International Search Report and Written Opinion for PCT Application No. PCT/US05/05521 mailed on Jan. 24, 2008.

Everdell, et al., "Improving Ocular Disease Screening by LED Illumination of the Eye"; Medical News Today; press release available online at http://www.medicalnewstoday.com/articles/199575.php on Sep. 1, 2010.

* cited by examiner

METHODS AND SYSTEMS FOR ENHANCED MEDICAL PROCEDURE VISUALIZATION

The present application claims the benefit of U.S. provisional application 60/546,843 filed Feb. 22, 2004, which is incorporated herein by reference in its entirety.

FIELD OF THE INVENTION

This invention relates generally to the field of medical and laboratory devices and more specifically to methods and systems for using image intensification for medical procedures within the human body. The methods and systems of the invention utilize infrared radiation (e.g. >750 nm) visualization of a surgical treatment area. Preferred methods and systems of the invention incorporate use of an infrared radiation visualization system which also are known as "night vision" systems.

BACKGROUND

Illumination of surgical treatment areas has been addressed generally through use of so-called light pipes or other visible light sources and camera apparatus. Light pipes have been used in ophthalmic surgeries. See, generally, U.S. Pat. No. 5,928,140. Camera-type apparatus have been in minimally invasive procedures such as arthroscopic and laparoscopic surgeries.

However, these existing approaches have notable drawbacks, including requiring surgeon to manipulate the light source device in addition to other surgical tools. Visible light sources also can potentially injure a patient's eye during ophthalmic procedures.

It thus would be desirable to have new methods and systems for visualizing surgical treatment areas. It would be particularly desirable to have new systems and methods for visualizing ophthalmic, arthroscopic and laparoscopic surgeries.

SUMMARY OF THE INVENTION

I now provide new systems and methods for visualizing treatment areas of a patient where the visualizing employs longer wavelength radiation (including infrared having a wavelength >750 nm or >800 nm) for visualization and/or illumination of the examined area.

Methods and systems of the invention are particularly useful for visualizing ophthalmic, arthroscopic and laparoscopic surgery areas as well as areas being examined by a medical professional but without necessarily surgery being performed, e.g. a patient's eye during an ophthalmic exam.

In preferred aspects, a night vision apparatus is used to view a surgical or other treatment area at infrared wavelengths.

More particularly, preferred methods of the invention include methods to view a patient area on which surgery or other medical examination is or will be performed, which comprises (a) viewing at a detection range of 750 nm or greater a targeted surgical area or patient area; and (b) performing a medical examination or surgical procedure within the viewed area, e.g. an ophthalmic, arthroscopic or laparoscopic procedure.

Methods of the invention thus can significantly minimize or effectively eliminate the need for a light source inside the patent body during medical procedures by amplifying the room's ambient light, by amplifying the extra ocular light source during ophthalmic procedures, or by amplifying the light from an external light source.

In accordance with the invention, a targeted surgical or other medical examination area also may be filter illuminated with a radiation source that emits at wavelength(s) of about 750 nm or greater, such as from 750 nm to 2000 nm, preferably about 800 nm to 850 nm. References herein to the optionally plural term "wavelength(s)" indicates that the radiation may be single wavelength or a spectrum of radiation having differing wavelengths.

Methods and systems of the invention provide a number of additional significant advantages including allowing the surgeon to utilize his or her surgical hand, typically utilized for the holding of a light source, for another instrument (bi-manual surgery) or other purpose.

Methods and systems of the invention are particularly useful for ophthalmic procedures. For instance, in current procedures using visible light illumination, a patients eye must be dilated to counter the contraction induced by the bright, illuminating visible light. In methods and systems of the invention, induced pupil dilation is not required. Thus, any need for dilating medication, such as cycloplegic eye drops can be obviated.

Methods and systems of the invention that utilize infrared radiation for visualization (rather than visible light) also can minimize patient discomfort associated with prior use of bright visible light during ophthalmic exams, especially for children and adolescent patients.

Methods and systems of the invention also can reduce the chance of retinal photic injury caused by excessive visible light exposure to the retina during surgery by minimizing or removing visible light during the procedure.

In another aspect of the invention new classes of dyes or chemicals are provided that can fluoresce or otherwise visualize under infrared spectra within the body, when used with infrared intensification apparatus in accordance with the present invention, for the purpose visualizing, identifying or assessing different biological tissues or structures of the body.

In accordance with a preferred embodiment of the invention, there is disclosed a process for using image intensification (night vision technology) for medical procedures within the human body comprising one or more steps of: positioning the image intensification device between the subject and the observer, adding an infrared light source or a visible light source preferably a relatively low level visible light source to the area of interest either through the tissue, through an aperture, or from inside of the tissue, viewing, photographing or recording the biological tissue using low light, infrared-only light, or a combination of different light spectra, performing a procedure using low light levels, infrared-only light levels, or a combination of the two, and optionally using certain chemicals or dyes that stain or combine with a biological tissue or structure of interest and fluoresce the tissue or structure under infrared or ultraviolet light with the image intensification apparatus.

In accordance with a preferred embodiment of the invention, there is disclosed a process for using image intensification with a microscope.

In accordance with a preferred embodiment of the invention, there is disclosed a process for using dyes, stains or chemicals that fluoresce under infrared spectra of the body, when used with infrared intensification visualization of the present invention, for the purpose of visualizing, identifying or assessing different biological tissues or structures of the body.

Methods and systems of the invention can be utilized e.g. in hospitals, ophthalmology clinics, operating rooms, office operating rooms, laboratories, vivariums, remote inspection kiosks for photographing people's eyes, or procedures performed away from the hospital in a public setting. Furthermore, methods and systems of the invention may by useful to the military in order to perform field inspections or medical procedures during combat without the use of white light that may alert enemies to their location.

In another aspect of the invention, a microscope is provided and is adapted for viewing images in the substantial absence of visible light having a wavelength of less than 750 nm. The microscope suitably comprises an image intensification apparatus and may include an infrared (such as >750 nm or >800 nm) radiation source to illuminate a specimen to be viewed by means of the microscope. In a preferred aspect, the microscope is retrofitted or otherwise comprises a night vision apparatus to facilitate viewing a specimen in the substantial absence of visible light (e.g. without any added illuminating visible light, or a viewing area such as a darkened room where ambient visible light has been excluded).

Infrared active dyes of the invention also will be particularly useful with such microscope and can be used to stain selectively specimens being viewed.

Other aspects and embodiments of the invention are discussed infra.

DETAILED DESCRIPTION OF THE INVENTION

Figure 1:
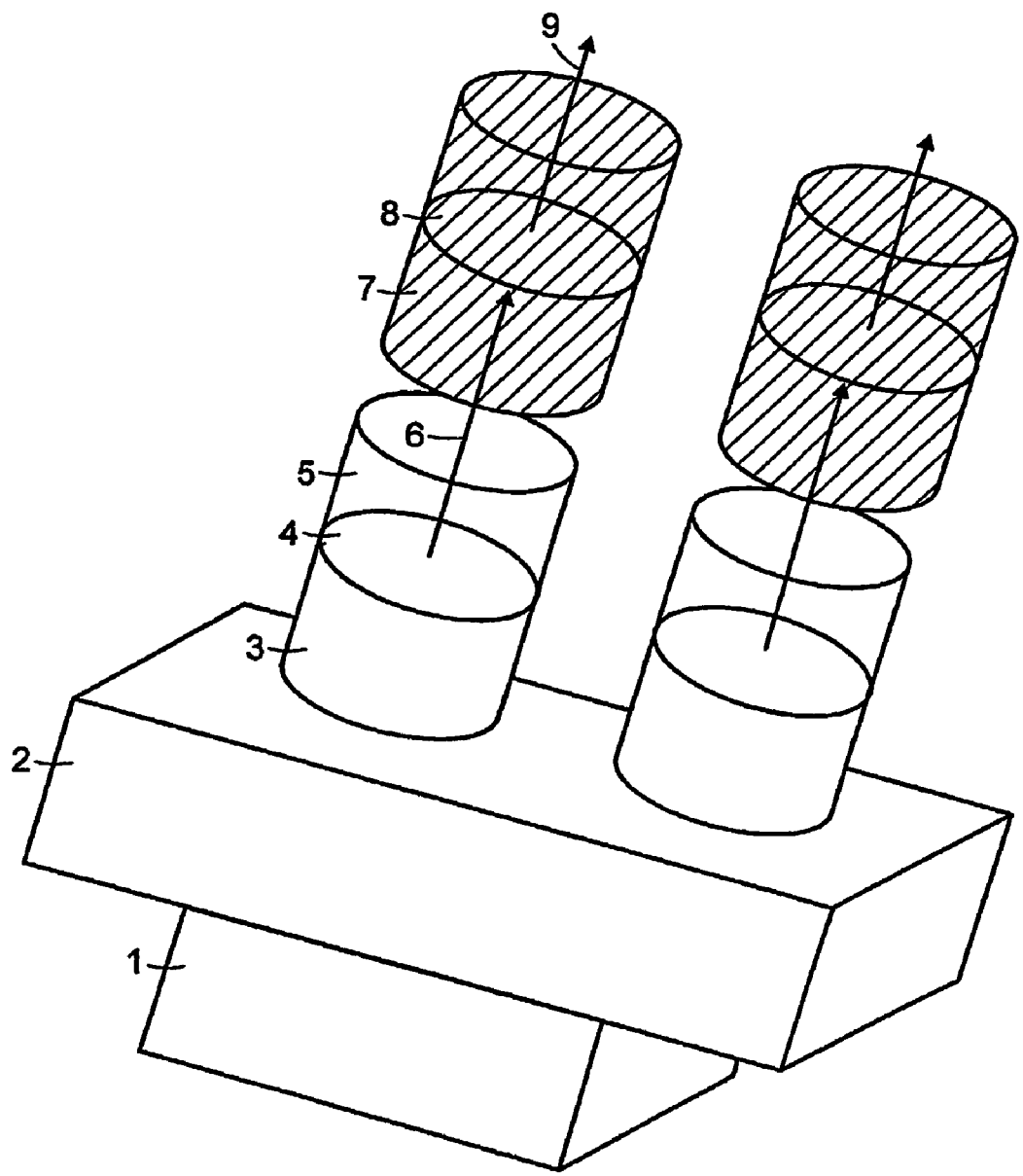
FIGS. 1 through 3 depict preferred visualization systems of the invention.

As discussed above, methods and systems of the invention include use of image intensification equipment, otherwise known as night vision tubes, to amplify visible or infrared light for e.g. medical or research personnel such as an ophthalmologist, surgeon, physician, optometrist, researcher or technician for the purpose of visualizing closed environments inside humans and animals, particularly, but not limited to, the eye, during medical or other scientific procedures.

As also discussed above, methods and systems of the invention are particularly useful for visualizing radiation having wavelength longer than the visible spectrum (the visible spectrum being approximately from 400 nm to 700 nm). Thus, methods and systems of the invention are useful for visualizing infrared radiation, which can be from 750 nm to 1 mm, more typically 750 nm to 1 millimeter, even more typically 750 nm to 2000 nm. Many suitable infrared light sources that may be used for illuminating a surgical area in accordance with the invention will emit at between about 800 nm and about 850 nm. More particularly, many preferred filters and infrared radiation sources used for illumination of surgical areas in accordance with the invention emit radiation at 840 nm wavelengths.

Image intensification systems, also known as night vision, provide the viewer with electronically enhanced viewing. The image intensifier tubes do not show the actual object, but an enhanced image of that object. An important aspect of an night vision system can be an image intensifier tube.

The intensifiers are rated as either first, second or third generation, but the technology is improving quickly, and new generations are being developed. Image intensifier tubes basically comprise a photocathode which converts light images to electron images (these, in turn can be amplified); and a microchannel plate (in the second and third generations), which converts the flow of electrons back to a light image.

The first generation image intensifier tubes, or gen 1 as they are known, uses simple grid shaped electrodes to accelerate the electrons through the tube. The second and third generations of tubes (generation two and generation three) use complex microchannel plates (MCP) that not only accelerate the electrons pulled from the photocathode, but increase their number. This increased charge then causes the phosphors to glow more brightly in response to the light reflected.

As a result one can see more light at the viewing end of a second or third generation tube for a given light level. Second and third generation tubes also generally exceed first generation tubes in their ability to resolve detail, can eliminate image distortions and can have longer useful tube life.

Night vision products are available in variety of forms including, binoculars, hand held viewers, goggles, telescopes and rifle mounted scopes. Some of them are camera and/or video adaptable as well.

An important feature of an image intensification system is an image intensifier tube that amplifies the light in real-time that is focused on its input window from the microscope, telescope, or non-magnified tube. The image is amplified or intensified by approximately 50,000 times under current technology, but as image intensification technology improves, the amplification and spatial resolution also is will anticipated to improve. The amplified image is displayed in real-time (not interlaced or rasterized like a CCD camera) on the rear or output end of the tube called the phosphor screen, which can easily be seen by the viewer's eye, a 35 mm camera or a CCD camera or video. Using the night vision technology, the viewer is able to perform a medical or laboratory procedure without the use of a secondary visible light.

Arthroscopy is a surgical procedure used to look inside a joint. When performing arthroscopic surgery, the surgeon can see inside the joint with a small camera. The use of an infrared image intensification technology in combination with this camera could allow the elimination of a light, the amplification of existing light, or the surgeon to use a smaller infrared light source instead of the larger fiber optic "light pipe" currently used.

Microscopes are designed to use visible light for normal use, however image intensifier tubes can allow a viewer to look at objects in the dark. This can be useful for a researcher studying photo-sensitive organisms, a retinal surgeon concerned about light injury to the retina or other types of surgeons that want to amplify the current amount of light in the eye.

As discussed above, in another aspect of the invention new classes of dyes or chemicals are provided that fluoresce under infrared spectra of the body, when used during the infrared intensification apparatus of this patent, for the purpose visualizing, identifying or assessing different biological tissues or structures of the body.

A dye composition can be administered to a targeted patient area (i.e. tissue that is desired to be stained) by any number of approaches, e.g. an aqueous formulation or solvent-containing (e.g. alcohol-containing) formulation containing one or more dye compounds can be administered to a patient by injection, spray, drops or the like directly onto the tissue or area to be visualized, or other known administration routes.

Preferred dyes of the invention include those that are active (i.e. can be excited) within the spectrum of Ultraviolet light (10 nm and 400 nm), Visible light (400 nm to 700 nm), or infrared light (700 nm to 1 mm) for the purpose of the dye's emission of light in the lower energy state (longer-wavelength) of infrared (700 nm to 1 mm.)

Fluorescent dyes with longer wavelength absorption and emission are particularly useful in conjunction with materials of biological origin such as blood, urine, fecal matter, cells and tissues, where background or inherent fluorescence or absorption often interferes with detection of the added fluorescent dye. Furthermore, biological specimens often have decreasing levels of both absorption and fluorescence emission as the illumination energy approaches the infrared. In addition, numerous biological and nonbiological applications of long wavelength dyes exist, including use as laser dyes, or in electronics as optical memory elements using relatively low cost illumination sources such as laser diodes. Consequently, dyes that possess these spectral properties have potential utility in biological and non-biological applications.

Dyes of the invention preferably exhibit long wavelength emission bands, thereby showing enhanced utility in sample systems that possess trasparency primarily in the infrared region, or during the use of infrared wavelengths with infrared microscope, or infrared image intensification tubes.

Any particular dye compound can be readily evaluated empirically, e.g. applied to targeted tissue and view the dye under infrared radiation (e.g. radiation having wavelength of 800 nm to 2000 nm) to determine if the dye stains and visualizes effectively.

Suitable dyes for use in methods and systems of the invention will include cyandine dyes such as indocyanine green (has a peak absorption at about 800 nm; Molecular Weight: 774.97; Chemical Formula: $C_{43}H_{47}N_2NaO_6S_2$), naphthalocyanine dyes; and R-phycoerythrin and allophycocyanin (have fluorescence emissions within the infrared spectrums).

Other suitable dyes for use in the methods and systems of the invention include Trypan blue; and phycobiliproteins dyes.

Fluorescent proteins dyes also will be useful such as Green Fluorescent Proteins (GFP)—engineered variants of *Aequorea Victoria*; *aequorea*-derived fluorescent proteins (AFP)—new variants of green fluorescent proteins; and Red Fluorescent Proteins (RFP).

Additional useful dyes will be fluorescein dyes and methal complex dyes. Suitable metal complex dyes include Ni complex dye, phthalocyanine-metal complex dye, palladium dye, quinoid dyes.

Yet additional suitable dyes for use in the methods and systems of the invention include metallized azo dyes are useful as infrared absorptive dyes.

Also suitable are dyes having a dipyrromethenboron difluoride core structure, e.g. dipyrromethenboron difluoride dyes incorporating fused aromatic rings (dibenzopyrromethenboron difluoride dyes, structure shown below) are reported in U.S. Pat. No. 5,433,896 (1995).

Also suitable will be indole dyes including isoindole dyes such as 1-(isoindolyl)methylene-isoindole dyes.

Quantum Dots, nanometer-sized semiconductors and crystals with size tunable optical and electronic properties, can also be used to stain and visualize biological tissues as disclosed herein, and by altering the Quantum dot size and its chemical composition, fluorescence emission may be tuned from 400 nm to 2,000 nm wavelengths. Furthermore, quantum dots can be conjugated to proteins, antibodies, peptides, and poly-ethylene glycol (PEG-alation) for tissue targeting during visualization. Quantum dots can be covalently linked with biorecognition molecules such as peptides, antibodies, nucleic acids, and small molecules for use as fluorescent probes in the infrared and near-infrared wavelength. Examples of quantum dots include a cadmium selenide CdSe core which can be further capped with particles such as ZnS or CdS to electronically passify the surface, CdSe/ZnS.)

CdSe is normally passivated with zinc sulfide, resulting in a structure referred to as (CdSe)ZnS, or CdSe/ZnS, but zinc selenide and cadmium sulfide are also commonly used Hydrophobic surface ligands are replaced with bifunctional ligands such as mercaptoacetic acid, which contains a thiol group that binds strongly to the Quantum dot surface as well as a carboxylic acid group that is hydrophilic. Other functional groups may also be used; for example, silane groups can be polymerized into a silane shell around the Quantum dot after ligand exchange. In the second method, coordinating ligands (e.g., TOPO) on the Quantum dot surface are used to interact with an amphiphilic polymer (5, 35) such as octylamine-modified polyacrylic acid. These polymers may contain alkyl chains that are thought to interdigitate with hydrophobic TOPO ligands, leaving the hydrophilic carboxylic acid groups directed away from the Quantum dot surface. This later method is more effective than ligand exchange at maintaining the Quantum dot optical properties and storage stability in aqueous buffer, but it increases the overall size of Quantum dot probes.

Quantum dot may be used to improve the sensitivity and multiplexing abilities of in situ staining due to their emission brightness and narrow fluorescence spectra. By labeling nuclear antigens with green silica-coated (CdSe)ZnS Quantum dots and F-actin filaments with red Quantum dots in fixed mouse fibroblasts for example, these two spatially distinct intracellular antigens can be simultaneously detected.

Fluorescent proteins and small organic dyes have been used as fluorescent contrast agents for living animal imaging. By attaching tissue-specific peptides to the Quantum dot, these nanoparticles were targeted to the lung vasculature, tumor vasculature, or tumor lymphatic vessels.

Many types of Quantum dots have recently been developed with bright emission within the near infrared and infrared range (CdTe, CdSeTe, (CdTe)CdSe, PbS, PbSe QDs). PEG and other biologically inert polymers may be useful for rendering Quantum dots biocompatible.

The compounds listed in the following tables also will be useful dyes for methods and systems of the invention.

| Solvent Soluble Near Infrared Dyes | |
|---|---|
| Absorption (nm) | Chemical Formula |
| 775 | $C_{32}H_{36}ClN_2I$<br>Chemical Name: Near Infrared Laser Dye is 2-[2-[2-chloro-3-[(1,3-dihydro-1,3,3-trimethyl-2H-indol-2-ylidene)-ethylidene]-1-cyclohexen-1-yl]ethenyl]-1,3,3-trimethylindolium iodide]. This near infrared dye is highly soluble in alcohols and polar solvents, such as NMP, DMF and DMSO. |
| | |
| 775 | $C_{32}H_{36}Cl_2N_2O_4$ |
| 780 | $C_{36}H_{44}ClN_2I$<br>Chemical Name: 2-[2-[2-chloro-3-[(1,3-dihydro-3,3-dimethyl-1-propyl-2Hindol-2-ylidene)-ethylidene]-1-cyclohexen-1-yl]-ethenyl]-3,3-dimethyl-1-propylindolium iodide]. |

Solvent Soluble Near Infrared Dyes

| Absorption (nm) | Chemical Formula |
|---|---|

[Structure: bis-indolium cyanine dye with chlorocyclohexenyl bridge, N-propyl groups, iodide counterion]

| 780 | $C_{36}H_{44}Cl_2N_2O_4$ |
| 780 | $C_{34}H_{40}N_2O_6Cl_2$ |

Chemical Name: 2-[2-[2-Chloro-3-[(1,3-dihydro-3,3-dimethyl-1-(2-hydroxy)-ethyl-2H-indol-2-ylidene)-ethylidene]-1-cyclohexen-1-yl]ethenyl]-3,3-dimethyl-1-(2-hydroxy)ethyl-1H-idolium perchlorate

[Structure: bis-indolium cyanine dye with chlorocyclohexenyl bridge, N-(2-hydroxyethyl) groups, $ClO_4^-$ counterion]

| 798 | $C_{54}H_{54}N_2O_4S$ |
| 805 | $C_{35}H_{42}ClN_2I$ |
| 803 | $C_{35}H_{42}Cl_2N_2O_4$ |
| 815 | $C_{42}H_{44}ClN_2I$ |
| 813 | $C_{47}H_{47}ClN_2O_3S$ |

| Properties | Value |
|---|---|
| Absorption Maximum: | 813 nm (in MeOH) |
| Absorption Coefficient: | $2.48 \times 10^5$ l $mol^{-1}$ $cm^{-1}$ |
| Molecular Weight: | 755.43 g $mol^{-1}$ |
| Melting Point: | 222-224° C. (dec.) |
| Appearance: | Dark Brown Powder |
| Solubility: | 60 mg/ml (in $CH_3OH$) |

| 838 | $C_{46}H_{45}ClN_2O_3S$ |
| 905 | $C_{62}H_{96}N_6SbF_6$ |

| Properties | Value |
|---|---|
| Absorption Maximum: | 905 nm (in MeOH) |
| Absorption Coefficient: | $0.69 \times 10^6$ l $mol^{-1}$ $cm^{-1}$ |
| Chemical Formula: | $C_{62}H_{96}N_6SbF_6$ |
| Molecular Weight: | 1157.19 g $mol^{-1}$ |
| Melting Point: | 147-150° C. (dec.) |
| Appearance: | Dark Green Powder |
| Solubility: | 35 mg/ml (in $CH_3OH$) |

| 1060 | $C_{62}H_{92}N_6Sb_2F_{12}$ |

Chemical Name: N,N,N,N,-Tetrakis(4-dibutylaminophenyl)-p-benzoquinone bis(iminium hexafluoroantimonate)

[Structure: tetrakis(4-dibutylaminophenyl)-p-phenylenediamine dication with two $SbF_6^-$ counterions]

| 1075 | $C_{57}H_{48}N_4SbF_6$ |

Water Soluble Near Infrared Dyes

| Absorption (nm) | Chemical Formula |
|---|---|
| 781 | $C_{38}H_{46}ClN_2O_6S_2Na$ |

| Properties | Value |
|---|---|
| Absorption Maximum: | 780 nm (in MeOH) |
| Absorption Coefficient: | $2.00 \times 10^5$ l $mol^{-1}$ $cm^{-1}$ |
| Chemical Formula: | $C_{38}H_{46}ClN_2O_6S_2Na$ |
| Molecular Weight: | 667.12 g $mol^{-1}$ |
| Melting Point: | 232-234° C. (dec.) |
| Appearance: | Green Crystal |
| Solubility: | 60 mg/ml (in water) |

| 785 | $C_{48}H_{47}N_2O_6S_2Na$ |

| Properties | Value |
|---|---|
| Absorption Maximum: | 784 nm (in $CH_3OH$) |
| Absorption Coefficient: | $2.04 \times 10^5$ l $mol^{-1}$ $cm^{-1}$ |
| Chemical Formula: | $C_{43}H_{47}N_2O_6S_2Na$ |
| Molecular Weight: | 774.97 g $mol^{-1}$ |
| Melting Point: | 241-243° C. (dec.) |
| Appearance: | Dark Green Powder |
| Solubility: | 35 mg/ml (in water) |

| 791 | $C_{44}H_{52}N_3O_6S_3Na$ |
| 803 | $C_{38}H_{49}N_3O_6S_4Cl$ |
| 807 | $C_{36}H_{44}N_2O_6S_2Na$ |
| 822 | $C_{46}H_{51}ClN_2O_6S_2$ |

| Properties | Value |
|---|---|
| Absorption Maximum: | 822 nm (in $CH_3OH$) |
| Absorption Coefficient: | $2.40 \times 10^5$ l $mol^{-1}$ $cm^{-1}$ |
| Chemical Formula: | $C_{46}H_{51}ClN_2O_6S_2$ |
| Molecular Weight: | 827.49 g $mol^{-1}$ |
| Melting Point: | 253-255° C. (dec.) |
| Appearance: | Dark Green Powder |
| Solubility: | 30 mg/ml (in water) |

| 832 | $C_{52}H_{56}N_3O_6S_3Na$ |

Chemical Name: 2-[2-[2-(4-aminothiophenyl)-3-[[1,3-dihydro-1,1-dimethyl-3-(4-sulfobutyl)-2H-benz[e]indol-2-ylidene]ethylidene]-1-cyclohexen-1-yl]ethenyl]-1,1-dimethyl-3-(4-sulfonyl)-,inner salt, sodium salt -continued Water Soluble Near Infrared Dyes Absorption (nm) | Chemical Formula

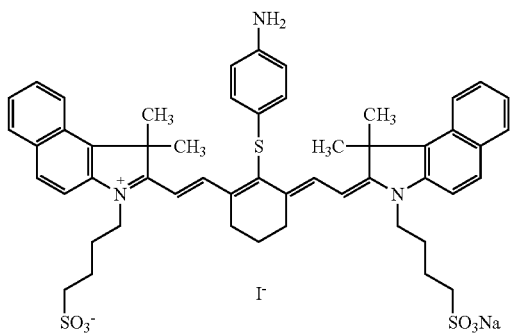

Metal Complex Near Infrared Dyes

| Absorption (nm) | Chemical Formula |
|---|---|
| 845 | $C_{28}H_{40}Cl_4NS_4Ni$ |
| 867 | $C_{28}H_{38}Cl_6NS_4Ni$ |
| 882 | $C_{32}H_{28}S_4Ni$ |
| 885 | $C_{32}H_{26}O_4S_4Cl_2$ |
|  | Chemical Name: Bis(3,4-dimethoxy-2-chlorodithiobenzil)nickel |

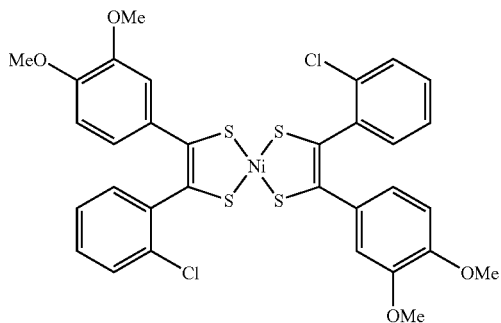

| | |
|---|---|
| 892 | $C_{30}H_{48}NS_4Ni$ |
| 922 | $C_{32}H_{28}O_4S_4Ni$ |
| 990 | $C_{32}H_{30}N_2S_4Ni$ |

Referring now to the drawings, FIG. 1 shows an image intensification apparatus comprising a microscope base 1 and microscope head 2 with an objective 3 and lens 4. In the present form of the invention, this microscope has a pair of image intensification tubes 7, 8 attached to the microscope objectives 5. It is a feature of the invention that light 6 passes through the lenses of the microscopes, and is amplified to a much brighter image 9 for the viewer to see. This figure shows two night vision tubes in order to exhibit stereo, however, the invention can also be with a single tube.

Figure 2:
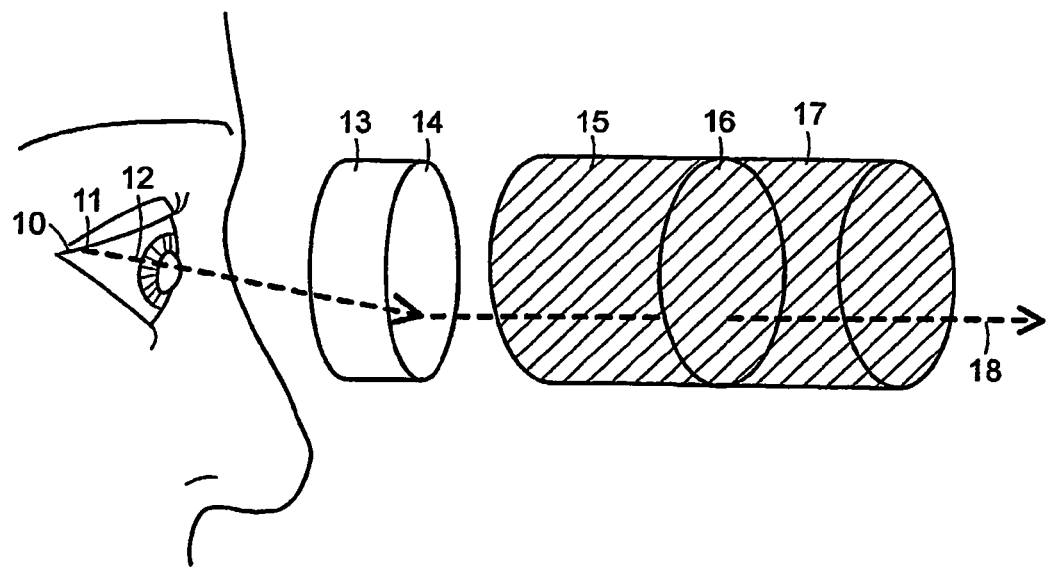

In accordance with a further aspect of the invention, FIG. 2 shows an example of using image intensification tubes during an ophthalmic inspection of the human eye. In the depicted form of the invention, physician or technician or other user can use image intensification equipment with other lenses to examine features of a patient's eye 10. By positioning the apparatus between the subject and the viewer, the viewer can view the area of interest 11 that is demonstrated inside the eye 10 through the patient's pupil 12 and through a lens 13, 14. The lens focuses the image onto the image intensification tube 15, and amplifies the light 16, 17 into a brighter, image using visible light 18 for the viewer to see.

Figure 3:
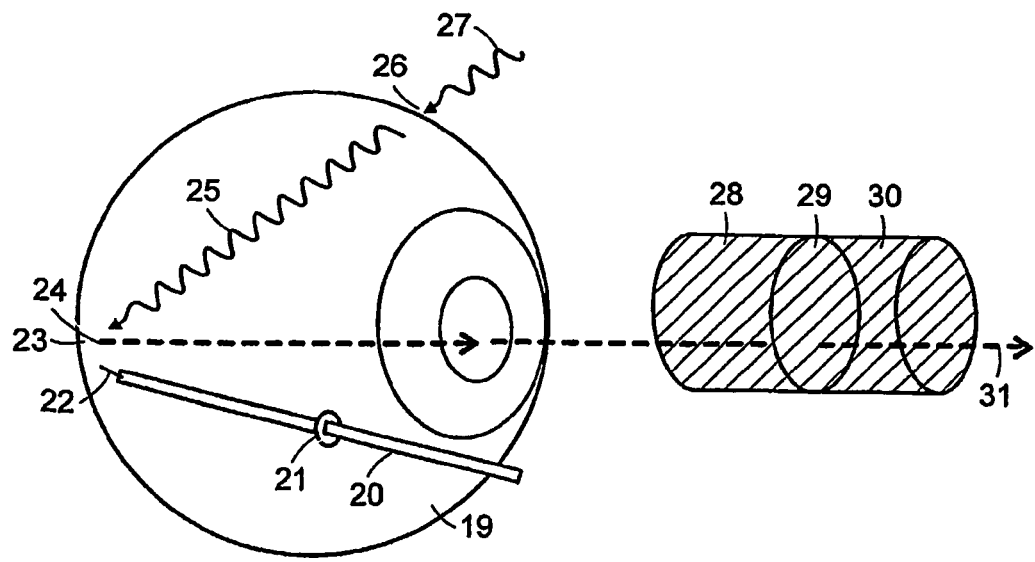

FIG. 3 shows use of image intensification tubes during surgery. Although FIG. 3 shows an eye 19, this could represent any cavity of the body, except that a camera would be used rather than directly viewing through the pupil. A surgical probe 20, such as scissors, forceps, picks, or other devices, is inserted through cannula 21 into the eye, with the tip 22 performing a procedure on the area of interest 23. The image is viewed directly 24 by the surgeon through an opening, or in the case of laparoscopic or arthroscopic surgery or other such medical procedure, through a camera in combination with image intensification. Infrared light 25, or other types of light, is shown either directly through the eye 26, 27 or shown though another cannula or directly through an opening such as through the pupil. The image 24 is captured and focused by the image intensification tubes 28, 29, 30, and the image is amplified into visible light 31 for the viewer. As discussed above, one or more stains (dyes) may be used in combination with these procedures to fluoresce certain biological structures or membranes at the area of interest such as 23.

All documents mentioned herein are incorporated by reference herein in their entirety.

The foregoing description of the invention is merely illustrative thereof, and it is understood that variations and modifications can be effected without departing from the scope or spirit of the invention as set forth in the following claims.

What is claimed is:

1. A method for viewing an ophthalmic surgical area in a human eye on which surgery is or will be performed, or for viewing the ophthalmic surgical area otherwise being examined by a medical professional, comprising:
   directing, using a radiation source apparatus, infrared radiation having wavelength(s) of about 750 nm or greater into the ophthalmic surgical area;
   visualizing the ophthalmic surgical area in the substantial absence of visible light having a wavelength of less than about 750 nm, through using an imaging apparatus capable of generating an anatomical tissue surface image of the ophthalmic surgical area under such light conditions by only detecting the infrared radiation that is directed into the ophthalmic surgical area and that is naturally reflected from the ophthalmic surgical area; and
   performing an ophthalmic procedure on the ophthalmic surgical area or examining the ophthalmic surgical area using the visualizing of the ophthalmic surgical area in the substantial absence of visible light,
   wherein the imaging apparatus is a night vision viewing apparatus comprising an image intensifier tube.

2. The method of claim 1, wherein the radiation source apparatus and the imaging apparatus are part of a single device.

3. The method of claim 1, wherein the directing comprises directing infrared radiation having wavelength(s) of from about 800 nm to 850 nm.

4. The method of claim 1, wherein the imaging apparatus employed to view the ophthalmic surgical area is an image intensification apparatus.

5. The method of claim 1, wherein the night vision viewing apparatus further comprises a microscope for magnifying the ophthalmic surgical area.

6. The method of claim 1, wherein the performing comprises performing an ophthalmic procedure.

7. A method for viewing an ophthalmic surgical area in a human eye on which surgery is or will be performed, comprising:
- directing, using a radiation source apparatus, infrared radiation having wavelength(s) of about 750 nm or greater into the ophthalmic surgical area;
- visualizing the ophthalmic surgical area in the substantial absence of visible light having a wavelength of less than about 750 nm, through using an imaging apparatus capable of generating a visual anatomical tissue surface image of the ophthalmic surgical area under such light conditions by detecting only the infrared radiation directed into ophthalmic surgical area by the radiation source apparatus that is reflected from the ophthalmic surgical area; and
- performing an ophthalmic procedure within the viewed ophthalmic surgical area in the substantial absence of visible light,
- wherein the imaging apparatus is a night vision viewing apparatus comprising an image intensifier tube.

8. The method of claim 7 wherein one or more dye compounds that are visible in radiation having wavelength(s) of 750 nm or greater are applied to the ophthalmic surgical area.

9. A system for viewing an ophthalmic surgical area in a human eye on which surgery is or will be performed, or for viewing the ophthalmic surgical area otherwise being examined by a medical professional, comprising:
- an infrared radiation source apparatus to direct infrared radiation at the ophthalmic surgical area-having wavelength(s) of about 750 nm or greater and in the substantial absence of visible light having a wavelength of less than about 750 nm;
- a night vision viewing apparatus comprising an image intensifier tube and a detector apparatus receiving infrared radiation generated by the infrared radiation source apparatus that is reflected from the ophthalmic surgical area; and
- a display apparatus configured to display an anatomical tissue surface image of the ophthalmic surgical area using only the infrared radiation generated by the infrared radiation source apparatus that is reflected from the ophthalmic surgical area to view the ophthalmic surgical area at about 750 nm or greater while performing an ophthalmic procedure.

10. The system of claim 9 further comprising one or more dyes that are visible at 750 nm or greater.

11. The system of claim 10 wherein the one or more dyes are formulated for application to the ophthalmic surgical area.

12. A computer-implemented method for visualizing an ophthalmic surgical area comprising:
- transmitting infrared radiation from a visualization device into the ophthalmic surgical area;
- detecting reflected infrared radiation from the ophthalmic surgical area using a night vision viewing apparatus comprising an image intensifier tube and a detector;
- displaying an anatomical tissue surface image of the ophthalmic surgical area using only the transmitted infrared radiation that is reflected from the ophthalmic surgical area;
- wherein visible light is substantially absent at the ophthalmic surgical area.

13. A computer-implemented method of claim 12, wherein a surgical procedure is performed using the displaying of the anatomical tissue surface image of the ophthalmic surgical area.

14. The method of claim 1, wherein the ophthalmic surgical area is a contoured area comprising structures of the body.

15. The method of claim 1, wherein the ophthalmic procedure is a diagnostic procedure.

16. The method of claim 1, wherein the ophthalmic procedure is a surgical procedure.

17. The method of claim 1, wherein the ophthalmic procedure is a neuro procedure.

18. The method of claim 1, wherein the using the visualizing of the ophthalmic surgical area comprises using the visualizing of the ophthalmic surgical area in real-time.

19. The method of claim 1, wherein the visualizing the ophthalmic surgical area occurs without applying a compound to induce pupil dilation.

20. The method of claim 1, wherein the visualizing the ophthalmic surgical area occurs without the use of a dye compound.

* * * * *

UNITED STATES PATENT AND TRADEMARK OFFICE
CERTIFICATE OF CORRECTION

PATENT NO. : 8,050,745 B2
APPLICATION NO. : 11/508734
DATED : November 1, 2011
INVENTOR(S) : Sean Caffey et al.

It is certified that error appears in the above-identified patent and that said Letters Patent is hereby corrected as shown below:

On Page 1 (Item 74), Line 1, change "Olson" to --Olson,--.

In Column 2, Line 4, change "filter" to --further--.

In Column 2, Line 18, change "patients" to --patient's--.

In Column 3, Line 4, change "by" to --be--.

In Column 5, Line 17, change "trasparency" to --transparency--.

In Column 5, Line 26, change "cyandine" to --cyanine--.

In Column 5, Line 39, change "methal" to --metal--.

In Column 6, Line 3, change "used" to --used.--.

In Column 6, Line 64, change "2Hindol" to --2H-indol--.

In Column 7, Line 27, change "idolium" to --indolium--.

In Column 7, Line 28-35 (Approx.), see discrepancy below.

Change " 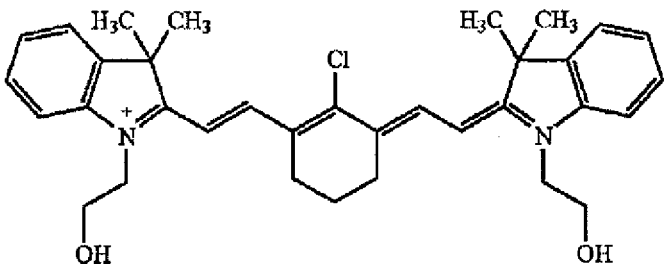 "

Signed and Sealed this
Tenth Day of April, 2012

David J. Kappos
*Director of the United States Patent and Trademark Office*

CERTIFICATE OF CORRECTION (continued)
U.S. Pat. No. 8,050,745 B2 to --
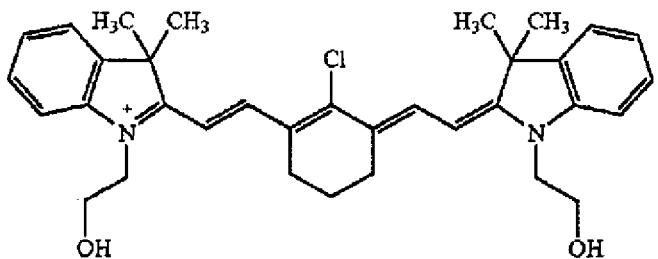
--.

In Column 7, Line 43 (Approx.), above "Absorption Maximum: 813 nm (in MeOH)" insert --Properties    Value--.

In Column 7, Line 46 (Approx.), above "Molecular Weight:    755.43 g mol$^{-1}$" insert --Chemical Formula:    $C_{47}H_{47}ClN_2O_3S$--.

In Column 7, Line 54 (Approx.), change "MeoH)" to --MeOH)--.

In Column 7, Line 55 (Approx.), change "$10^6$" to --$10^5$--.

In Column 8, Line 45 (Approx.), change "$C_{48}H_{47}N_2O_6S_2Na$" to --$C_{43}H_{47}N_2O_6S_2Na$--.

In Column 8, Line 53 (Approx.), change "$C_{36}H_{44}N_2O_6S_2Na$" to --$C_{36}H_{44}ClN_2O_6S_2Na$--.

In Column 8, Line 65 (Approx.), change "sulfonyl)-,inner salt," to --sulfonyl)-, inner salt,--.

In Column 9, Lines 7-20 (Approx.), See discrepancy below.

Change "
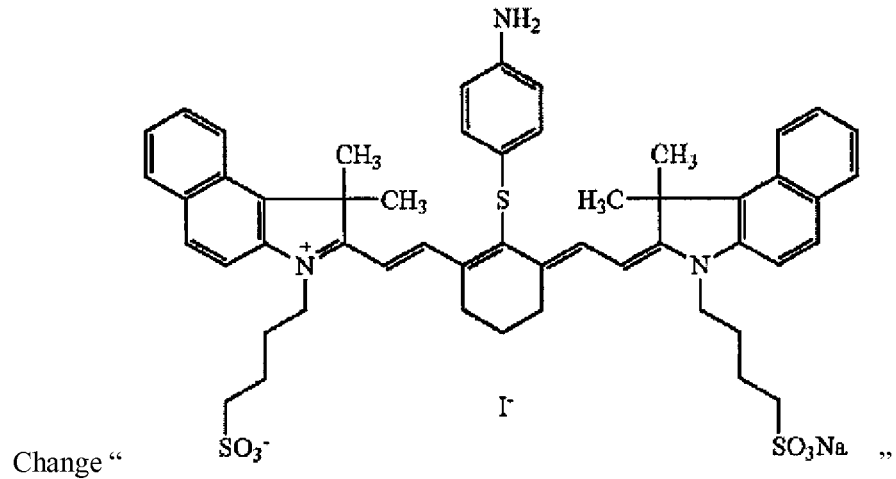
"

CERTIFICATE OF CORRECTION (continued)
U.S. Pat. No. 8,050,745 B2

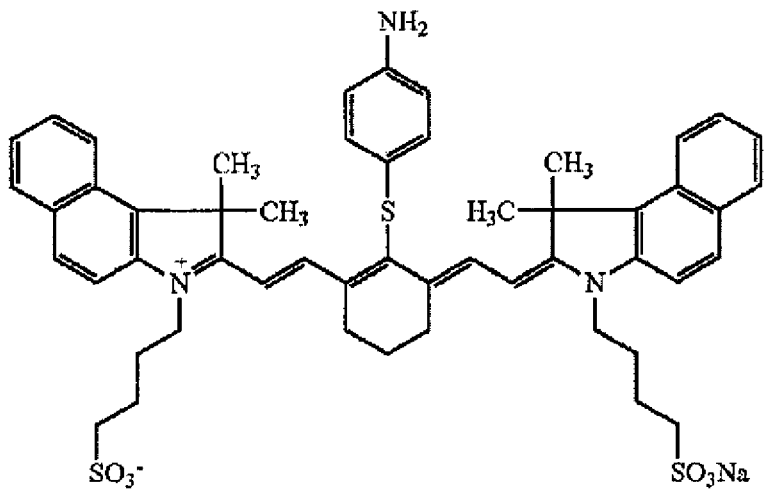

to -- --.

In Column 11, Line 11, in Claim 7, after "image" insert --excluding spectral imaging--.

In Column 11, Line 30, in Claim 9, change "area-having" to --area having--.